United States Patent [19]
Hansson

[11] Patent Number: 5,836,950
[45] Date of Patent: Nov. 17, 1998

[54] GUIDE INSTRUMENT

[76] Inventor: Henrik Lars Johan Hansson, Konsistoriegatan 6, Linköping, Sweden, S-582 22

[21] Appl. No.: 836,356
[22] PCT Filed: Nov. 21, 1995
[86] PCT No.: PCT/SE95/01379
   § 371 Date: May 13, 1997
   § 102(e) Date: May 13, 1997
[87] PCT Pub. No.: WO96/15727
   PCT Pub. Date: May 30, 1996

[30]    Foreign Application Priority Data

Nov. 22, 1994 [SE] Sweden .................................. 9404035

[51] Int. Cl.⁶ .................................................... A61B 17/76
[52] U.S. Cl. ................................................ 606/65; 606/96
[58] Field of Search .................................. 606/96, 97, 98, 606/86, 65, 66, 67, 68, 62, 63, 60

[56]         References Cited

U.S. PATENT DOCUMENTS

| 4,465,065 | 8/1984 | Gotfried | ..................................... 606/96 |
| 4,719,907 | 1/1988 | Banko et al. | |
| 5,152,764 | 10/1992 | Goble | ........................................ 606/96 |
| 5,429,641 | 7/1995 | Gotfried | ..................................... 606/67 |

FOREIGN PATENT DOCUMENTS

0 617 927 A1 | 10/1994 | European Pat. Off. .
2 271 800 | 12/1975 | France .

*Primary Examiner*—Guy V. Tucker
*Attorney, Agent, or Firm*—McCormick, Paulding & Huber

[57]            ABSTRACT

The present invention relates to a guide instrument which is adapted for use at operations for fixation of bone fragments at bone fractures, preferably femoral neck fractures, whereby the bone fragments are intended to be fixed relative to each other by means of at least two bone screws, whereby the guide instrument (1) is adapted for guiding a first and a second drill steel which are adapted for drilling passages in the bone fragments for the bone screws. The guide instrument (1) is designed to permit guiding of the drill steels, driving through of threaded front portions of the bone screws and guiding of uptapped or unthreaded rear portions of said bone screws.

15 Claims, 11 Drawing Sheets

GUIDE INSTRUMENT

This application is a 35 U.S.C. 371 application based on PCT/SE95/01379, filed Nov. 21, 1995.

BACKGROUND OF THE INVENTION

BRIEF DESCRIPTION OF THE DRAWINGS

The present invention relates to a guide instrument which is adapted for use at operations for fixation of bone fragments at bone fractures, preferably femoral neck fractures, whereby the bone fragments are intended to be fixed relative to each other by means of at least two bone screws, whereby the guide instrument is adapted for guiding a first and a second drill steel which are adapted for drilling passages in the bone fragments for the bone screws.

BRIEF DESCRIPTION OF THE INVENTION

At operations for fixation of bone fragments at fractures, it is important that the bone screws get exact predetermined positions relative to the bone fragments and to each other. For this purpose, bone screws are used having such through center-passages that they can be threaded onto wire-like guide means (so called guide wires). These wire-like guide means are drilled into the bone fragments during TV-roentgen control to exact positions, whereafter the bone screws are threaded onto the wire-like guide means so that said guide means guide said bone screws when said screws are driven into the bone fragments.

Since the wire-like guide means must have room in narrow center passages in the bone screws, they must be thin. This means that the guide means bend easy when they during drilling e.g. come across hard bone after having passed through softer cartilage portions. A wire-like guide means bent in this way during drilling, may lead to that the bone screw is difficult to advance, fasten or tighten and that it is guided to a wrong position. To remedy this problem by redrilling is time consuming and the redrilling can be complicated by the passage already drilled.

The use of wire-like guide means also requires cannulated bone screws, i.e. bone screws having longitudinal center passages, which means that the depth of the threads of the bone screws must be limited.

SUMMARY OF THE INVENTION

The object of the present invention is to remedy or eliminate this problem and this is arrived at according to the invention by means of a guide instrument having primarily the characterizing features of subsequent claim 1.

Since the guide instrument has said characterizing features, it renders it possible to carry through the operation without the use of wire-like guide means and thereby, avoid the problem that such guide means can complicate driving or tightening of the bone screw or guide said bone screw wrong during said driving or said tightening thereof. Furthermore, it is achieved, inter alia, that one can use bone screws without cannulae, i.e. without longitudinal center holes, which means that the threads of the screws can be made deeper and that drilling moments are eliminated during drilling.

BRIEF DESCRIPTION OF THE DRAWINGS

The invention will be further described below with reference to the accompanying drawings, wherein.

DETAILED DESCRIPTION OF THE DRAWINGS

The guide instrument 1 illustrated in the drawings is adapted to be used at operations for fixation of bone fragments 2, 3 at bone fractures, preferably femoral neck fractures. Hereby, the femoral neck 4 (collum) illustrated in the drawings has a fracture 5 and said bone fragment 2 consists of the bone on one side of the fracture 5, while the bone fragment 3 on the other side of the fracture 5 is the femoral head (caput).

The bone fragments 2, 3 are fixed relative to each other by means of bone screws 6, 7 and each such bone screw 6 and 7 has a threaded front portion 8 with external threads 9 and a rear portion 10 without threads.

Figure 6:
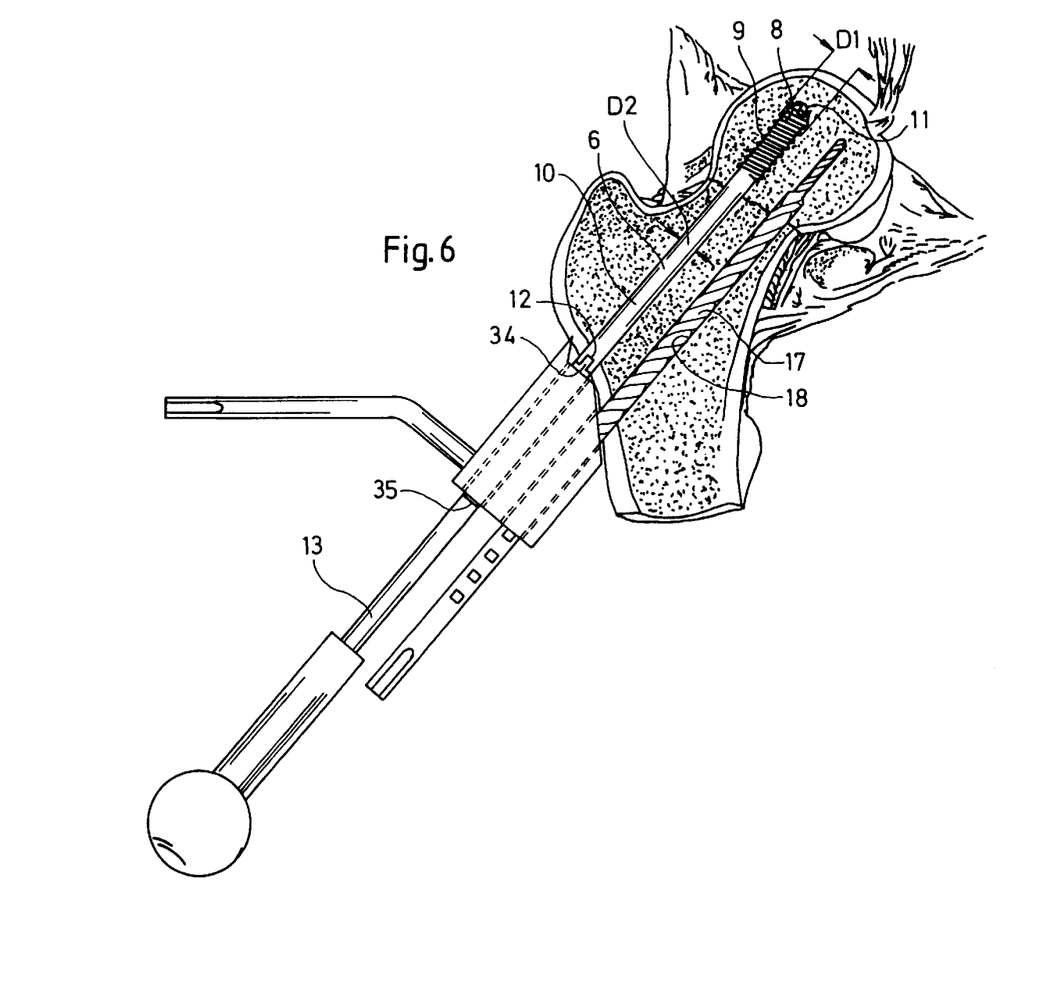
FIG. 6 is a side view of the guide instrument of FIG. 1 located in the guide position on said drill steel and while driving or tightening a bone screw.

Each bone screw 6, 7 is designed so that the outer diameter D1 of the external threads 9 is greater than the outer diameter D2 of the unthreaded or untapped portion 10 (see e.g. FIG. 6). The outer diameter D2 of the unthreaded portion 10 of every bone screw 6, 7 may e.g. be 6 mm or about 6 mm and the outer diameter D1 of the external threads 9 of each bone screw 6, 7 may be 8 mm or about 8 mm. Furthermore, each bone screw 6, 7 may have a total length of about 125 mm and the threaded front portion 8 thereof a length of about 20 mm.

Each bone screw 6, 7 has a point 11 with drilling properties and at the rear a transverse groove 12 for connection of a drive means 13 or 14. Each bone screw 6, 7 may also have a rear opening 15 with internal threads for fastening of a screw retainer 16 (see FIG. 11) which can be used for unscrewing the bone screw 6 or 7.

The bone screws 6, 7 are preferably solid in that respect that they have no longitudinal center passages extending therethrough (which has been necessary at those prior art bone screws which have been used in connection with wire-like guide means).

For carrying through the operation, one also uses a first drill steel 17 for drilling a first bone passage 18 in the bone fragments 2, 3 for one of the bone screws 6, 7 and a second drill steel 19 for drilling a second bone passage 20 in said bone fragments 2, 3 for another of said bone screws 6, 7. Each drill steel 17, 19 preferably has a point 21 with a smaller diameter D3 than the diameter D4 of the portions 22 of each drill steel 17, 19 located behind said point or tip 21. The diameter D3 of the point 21 is preferably about half as large as the diameter D4 of said portions 22. The diameter D3 may e.g. be 3,5 mm and the diameter D4 6,0 mm. The total length of said drill steel 17 and/or 19 can be about 210 mm and the length of said point 21 about 30 mm. Preferably, the first drill steel 17 can be somewhat shorter than the second drill steel 19.

In the guide instrument 1 there is drilled a first and a second passage 23 and 24, which extend in parallel with each other and which are open towards a rear side 25 as well as a front side 26 of the guide instrument 1. These passages 23, 24 are adapted to said drill steels 17, 19 so that said passages 23, 24 are fit for said drill steels 17, 19 and vice versa. Thus, the diameter D5 of each passage 23, 24 is only somewhat greater, preferably 0,1–0,4 mm greater that the largest diameters D4 of each drill steel 17 and 19. Thus, the diameter D5 of each passage 23, 24 may be 6,2 mm.

In said passages 23, 24 in the guide instrument 1, internal threads 27 and 28 respectively, are cut and these internal threads 27, 28 are adapted to the external threads 9 on the threaded front portions 8 of the bone screws 6, 7 so that said internal thread 27, 28 and said external threads 9 threadably slidably mesh with one another so that said portions 8 can be driven through the respective passage 23, 24.

The internal threads 27, 28 are preferably designed to that they guide the threaded front portion 8 of the bone screw 6, 7 driven through the respective passage 23, 24.

The largest diameter D6 of the internal threads 27, 28 is preferably only somewhat greater, e.g. 0,4–1,0 mm greater than the outer diameter D1 of the external threads 9 on the threaded portions 8 of the bone screws 6, 7. In the present embodiment, the diameter D6 may be e.g. 9,0 mm.

The first and second passages 23, 24 preferably have straight guide surfaces 29 in the longitudinal direction of said passages for guiding the drill steels 17, 19 and the untapped or unthreaded portions 10 of the bone screws 6, 7. These guide surfaces 29 preferably have a length L which is substantially greater, e.g. three times greater than the width B of that part of the internal threads 27, 28 which separates said guide surfaces 29 from each other. The guide surfaces 29 however, do not necessarily have to be straight, but may have an arcuate shape which is adapted to an arcuate shape between the external threads 9 of the bone screws 6, 7.

Each internal thread 27 and 28 respectively, runs preferably along a helical line 30 which extends around each passage 23 and 24 respectively, with at least four turns.

Figure 1:
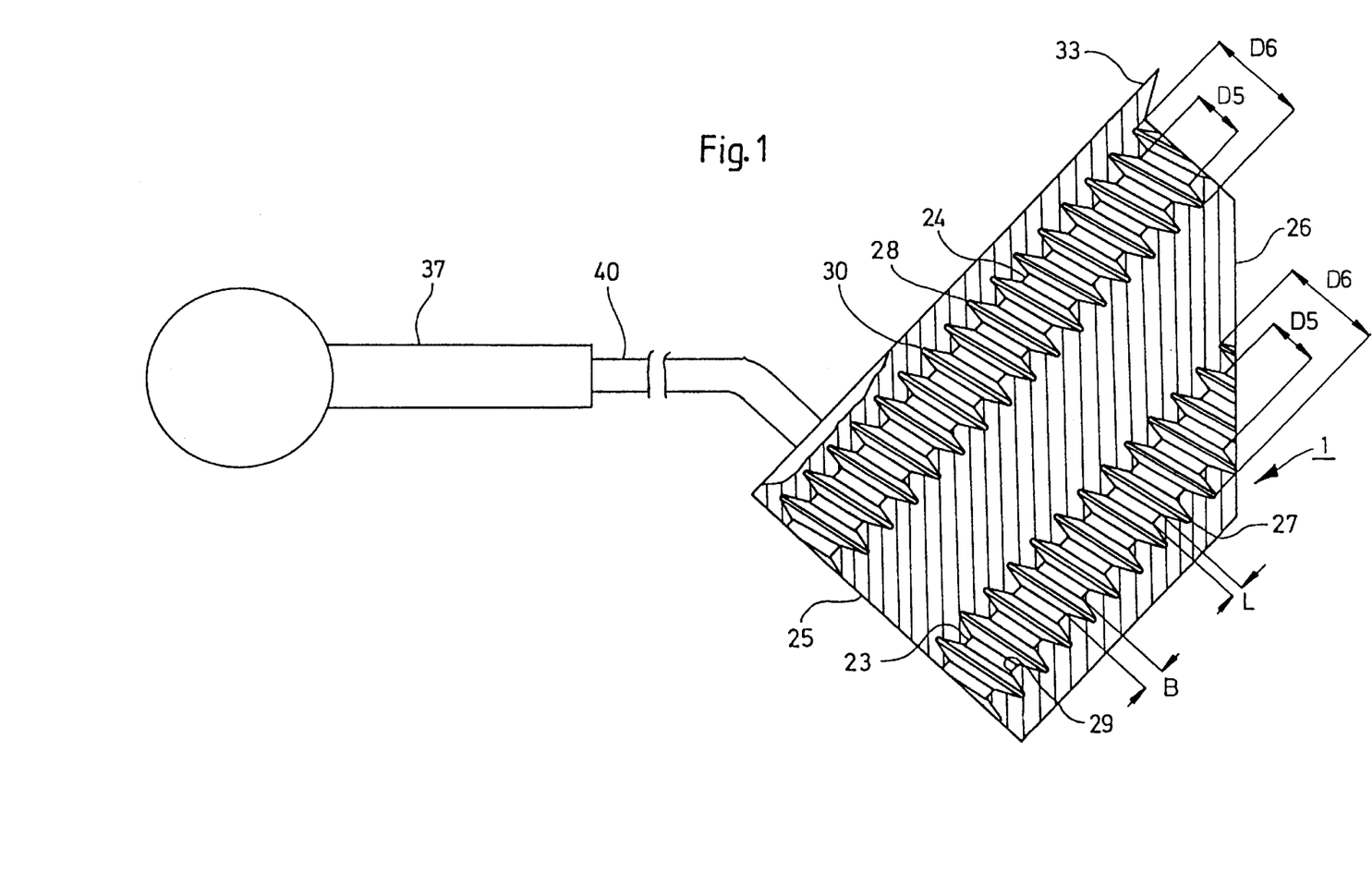
FIG. 1 is a section through a guide instrument according to the invention.

Preferably, only one internal thread 27, 28 runs around each passage 23, 24 from the inlet of said passage to the outlet thereof as is shown in FIG. 1.

Thus, in summary, it is apparent from the guide instrument 1 described above that the diameter D5 of each passage 23, 24 is adapted to the diameter D4 of each drill steel 17, 19 as well as to the diameter D2 of the untapped rear portion 10 of each bone screw 6, 7.

Thus, it is also apparent that the diameter D6 of the internal threads 27, 28 provided along each passage 23, 24 is adapted to the diameter D1 of the threaded front portion 8 of each bone screw 6, 7.

Hereby, the guide instrument 1 permits:

a) that the drill steels 17, 19 are guided by the bone passages 18, 20 during drilling;

b) that it can be fixedly attached to the drill steels 17, 19 before fastening or advancing the bone screws 6, 7;

c) that the bone screws 6, 7 can be driven therethrough for fastening in the bone fragments 2, 3; and d) that the untapped rear portions 10 of the bone screws 6, 7 are guided when the threaded front portion 8 of each bone screw 6, 7 is driven into each bone fragment 2, 3.

Figure 2:
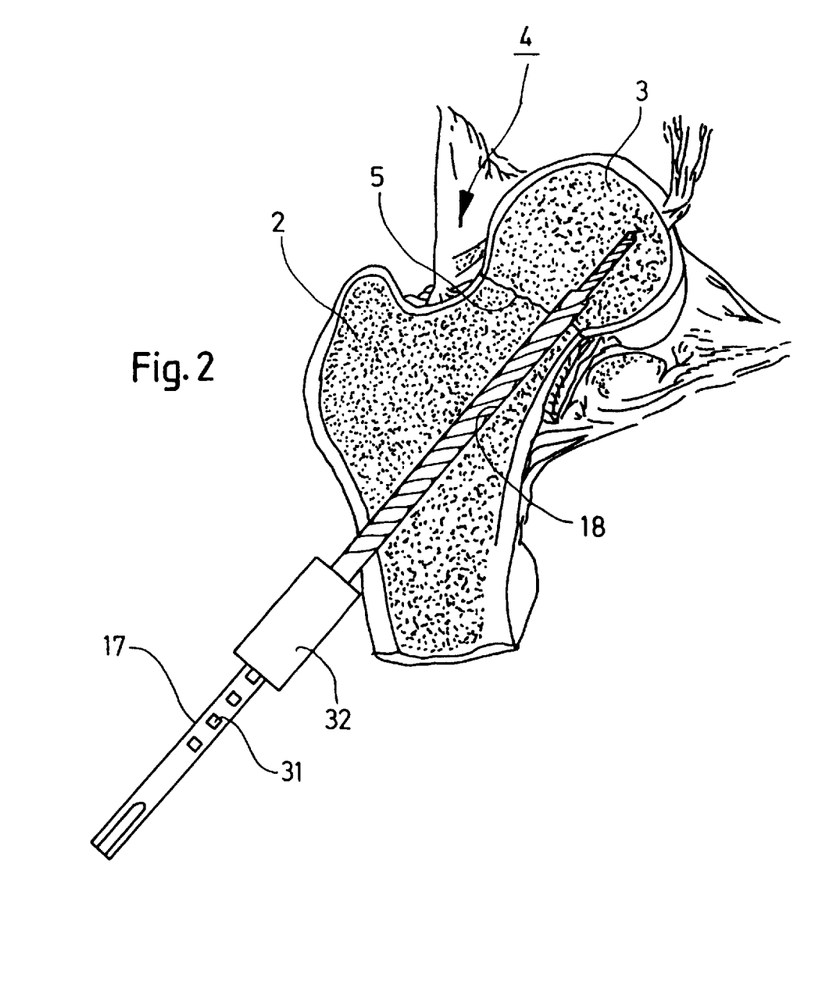
FIG. 2 is a side view of a drill steel which is used together with the guide instrument of FIG. 1 and which after drilling a passage in the bone fragment to be fixed, is retained in said bone fragment.
Figure 3:
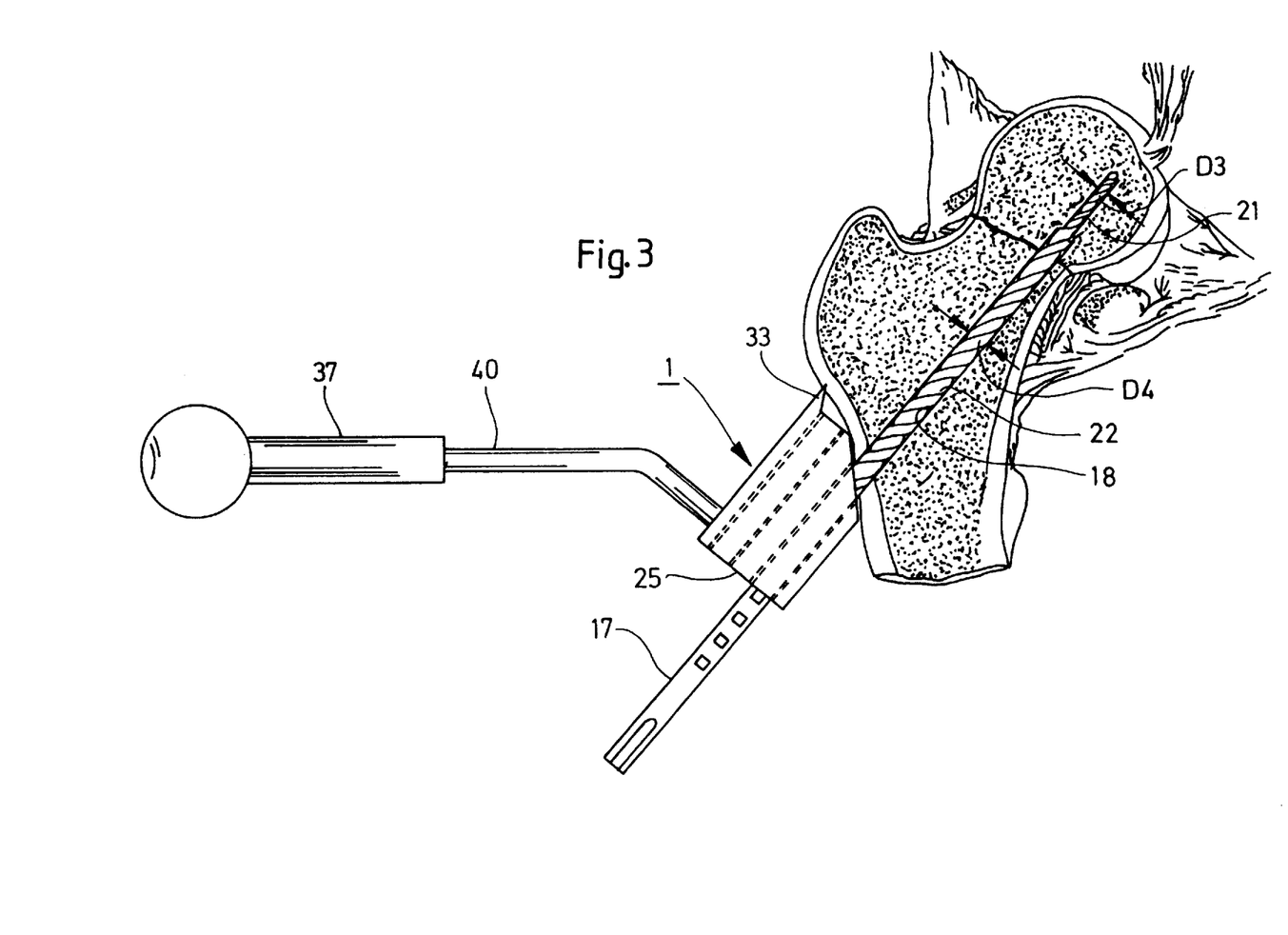
FIG. 3 is a side view of the guide instrument of FIG. 1 located on said drill steel in a guide position relative to said bone fragment.

The operation with the guide instrument 1 begins by drilling the first bone passage 18 (see FIG. 2) along the femoral neck 4 by means of the first drill steel 17. The drill steel 17 is provided with position marks 31 and a measuring sleeve 32 is threaded onto said drill steel and brought to engage the bone fragment 2. When a mark 31 during drilling is situated at the rear edge of the measuring sleeve 32, it is possible to determine how far into the bone fragment 3 the drill steel 17 has penetrated and to stop drilling at the correct depth.

When the first bone passage 18 has been drilled, the first drill steel 17 remains seated therein but the measuring sleeve 32 is removed from the drill steel 17. Thereafter, the guide instrument 1 is threaded onto the first drill steel 17 and fixedly attached to the bone fragment 2 in a predetermined position e.g. by bringing a fixation tip 33 into engagement with said bone fragment 2.

Figure 4:
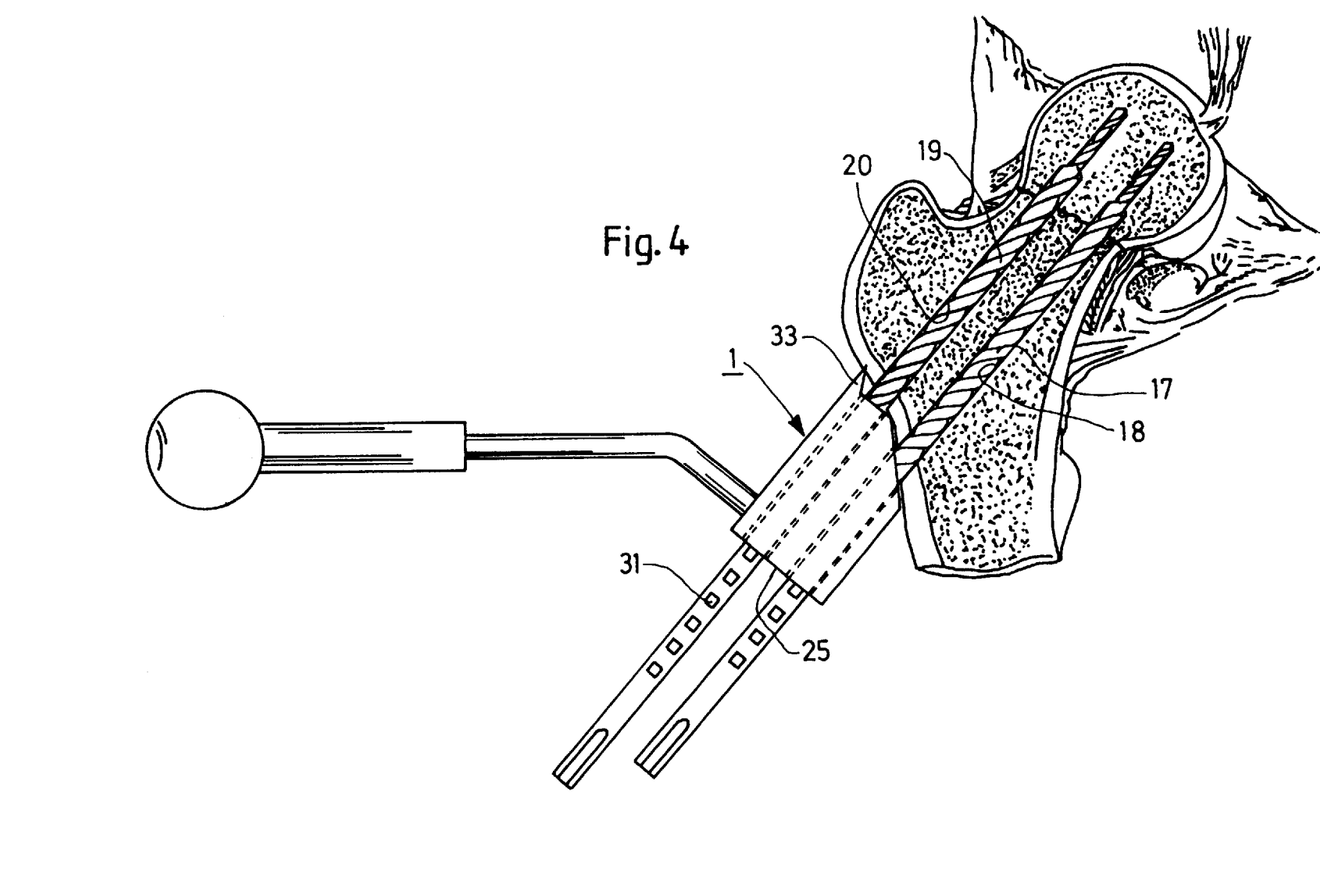
FIG. 4 is a side view of the guide instrument of FIG. 1 located in the guide position on said drill steel and while guiding of a second drill steel during drilling of a second bone passage.

When the guide instrument 1 has attained said predetermined position relative to the bone fragment 2 and is retained therein by the first drill steel 17 and the fixation tip 33, its second passage 24 is used for guiding the second drill steel 19 by means of which the second bone passage 20 is drilled (see FIG. 4). The bore depth of this second bone passage 20 is determined by comparing the position marks 31 on the second drill steel 19 with the rear or backside 25 of the guide instrument 1.

Figure 5:
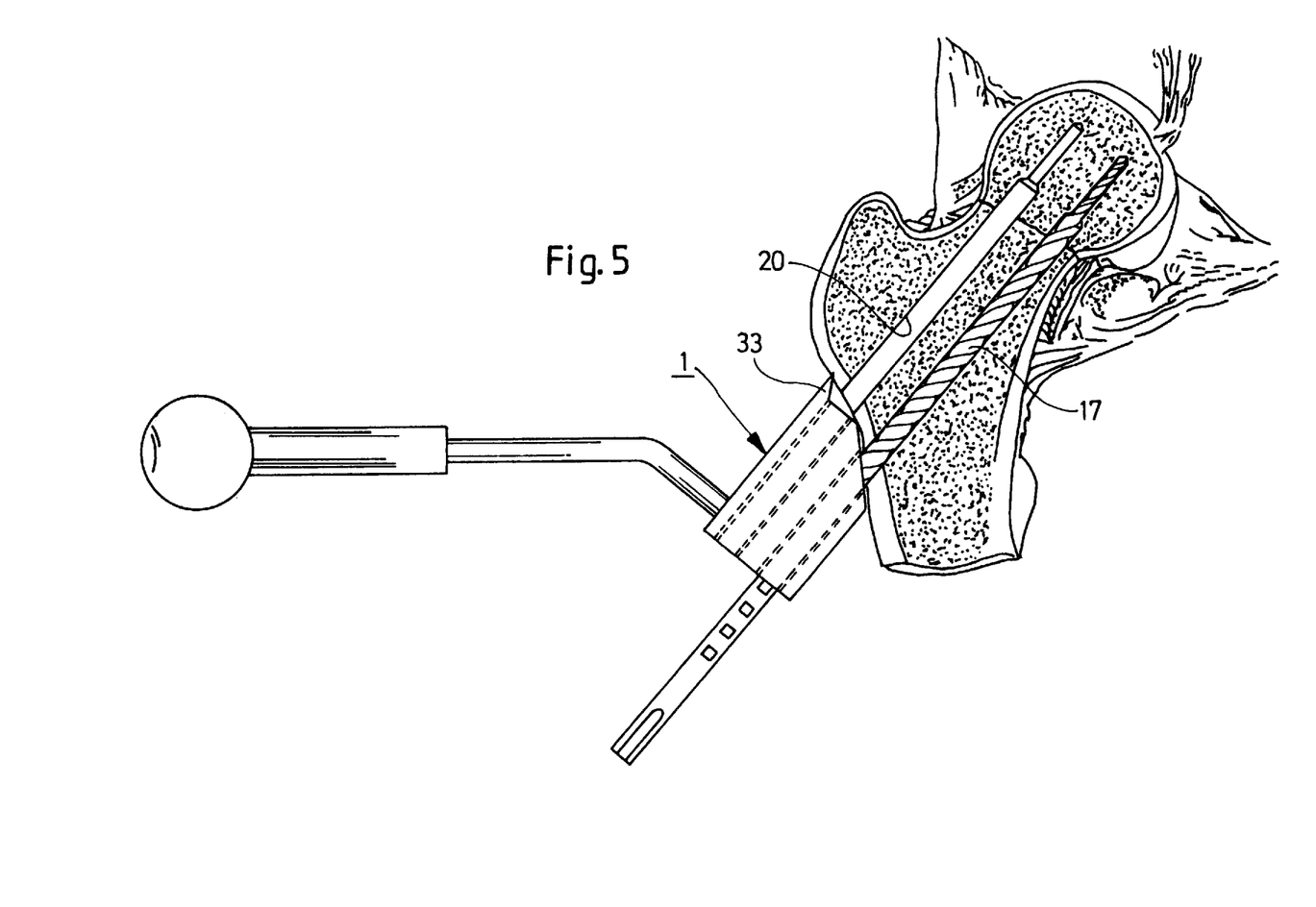
FIG. 5 is a side view of the guide instrument of FIG. 1 located in the guide position on said drill steel, whereby the second drill steel has been removed after drilling a second bone passage.

When the drilling of the second bone passage 20 is finished, the second drill steel 19 is removed and the guide instrument 1 is maintained in its guiding position by the first drill steel 17 and the fixation tip 33 (FIG. 5). If cortex or eventually any other part of the bone fragment 2 is hard, threads for the bone screw 6 can be cut in the bone passage 20 by means of a manually pivotable thread tap (not shown) which is driven through the second passage 24. Thereafter, the drive means 13 is connected with the bone screw 6 by inserting a transverse tongue 34 on said drive means 13 into the transverse groove 12 of the bone screw 6 and then, the bone screw 6 is driven by means of the drive means 13 through the second passage 24 of the guide instrument 1. Hereby, the threads 28 in the second passage 24 guide the threaded portion 8 of the bone screw 6 so that it is correctly oriented relative to the drilled second bone passage 20 when said threaded portion 8 leaves the second bone passage 20. When the bone screw 6 is driven so far into the second bone passage 20 that the threaded portion 8 thereof has left the guide instrument 1, the untapped or unthreaded portion 10 of the bone screw 6 is guided by the guide surfaces 29 of the second passage 24 so that said bone screw 6 is directed in parallel with the second bone passage 20 until said bone screw 6 is screwed home or tightened therein (FIG. 6). This can be determined by driving in the bone screw 6 so far that a position mark 35 on the drive means 13 (or a front position mark of two position marks 35, 36 on the drive means 13) is located at the backside 25 of the guide instrument 1.

Figure 7:
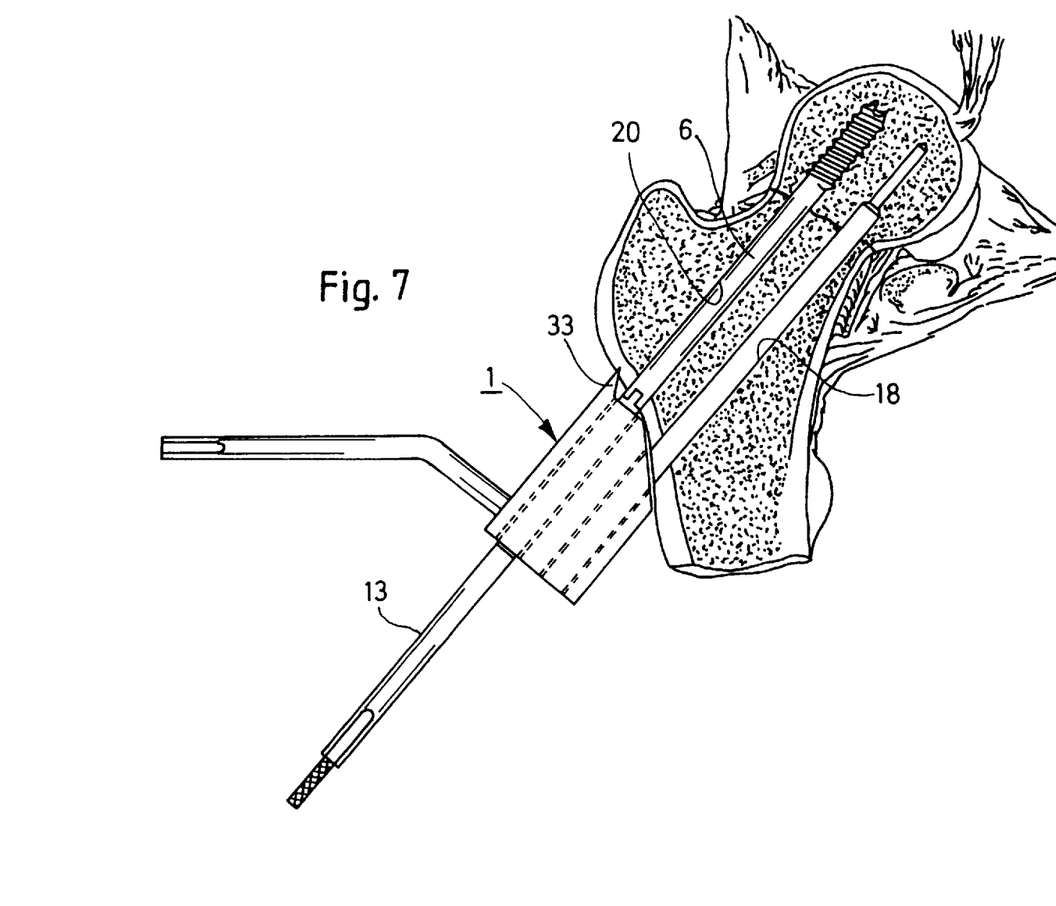
FIG. 7 is a side view of the guide instrument of FIG. 1 located in said guide position on a driving means by means of which a bone screw is advanced or fastened.

Then, the drive means 13 is left on the bone screw 6 so that said screw through its adaptation to the second passage 24 in the guide instrument 1, can retain said instrument in guide position along with its fixation tip 33 when the first drill steel 17 is removed from the first bone passage 18 and from the first passage 23 in the guide instrument 1 (FIG. 7). If cortex or eventually any other part of the bone fragment 2 is hard, threads for the bone screw 7 may then be cut by means of the abovementioned, manually pivotable thread tap, which in this case is driven through the first passage 23.

Figure 8:
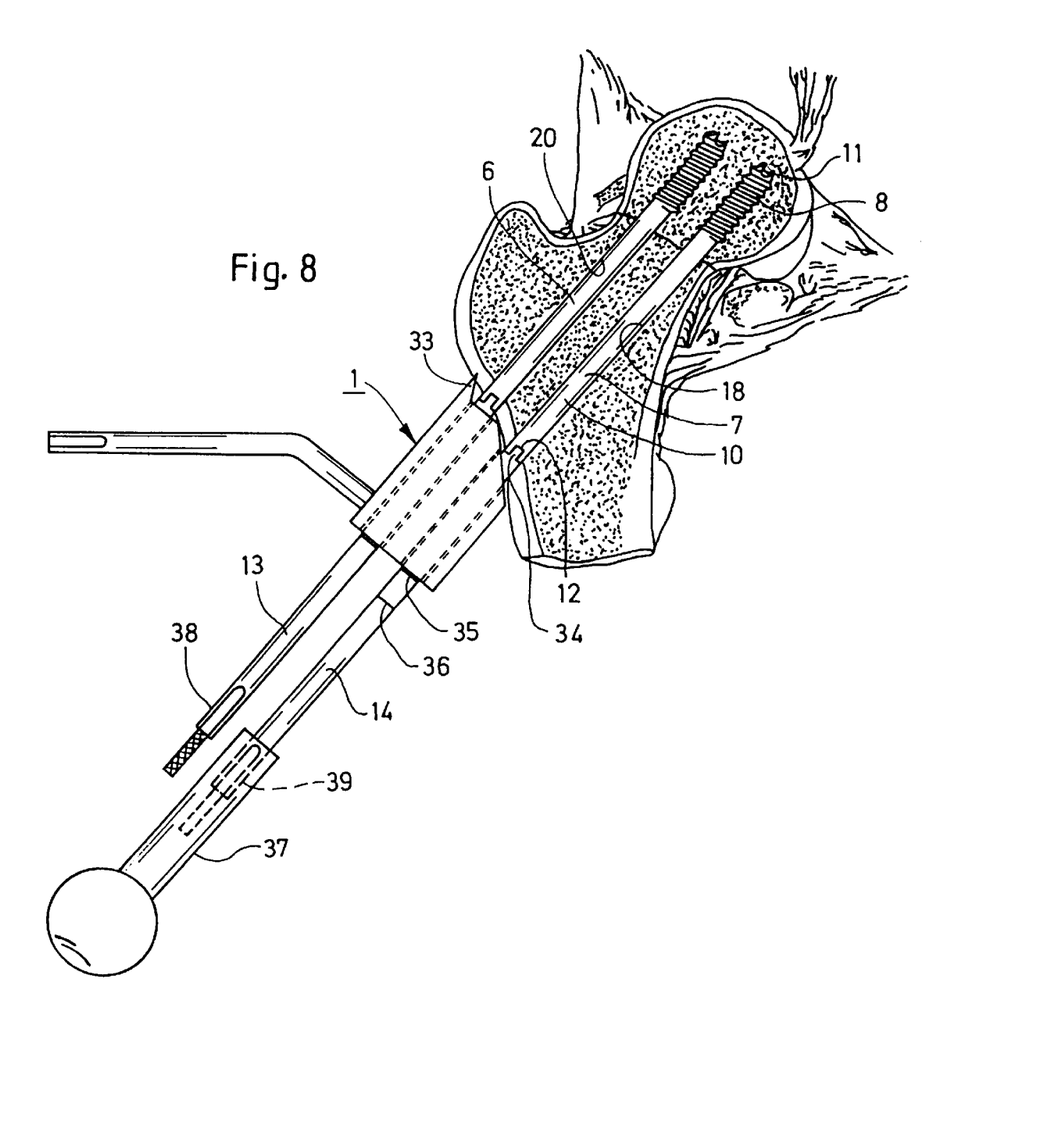
FIG. 8 is a side view of the guide instrument of FIG. 1 located in said guide position on said driving means and during fastening or tightening of a bone screw in a first bone passage.

Now, a transverse tongue 34 on the drive means 14 is connected with the transverse groove 12 of the bone screw 7 and said bone screw 7 is driven through the first passage 23 until it is screwed home or tightened in the first bone passage 18 (FIG. 8), which is the case when the position mark 35 on the drive means 14 is situated at the backside 25 of the guide instrument 1. During fastening or advancement, the threaded portion 8 of the bone screw 7 will be guided by the threads 27 in the first passage 23 and the untapped portion 10 of said bone screw 7 guided by the guide surfaces 29 in said first passage 23, so that said bone screw 7 is guided in parallel with the first bone passage 18 along the entire driving distance thereof.

Figure 9:
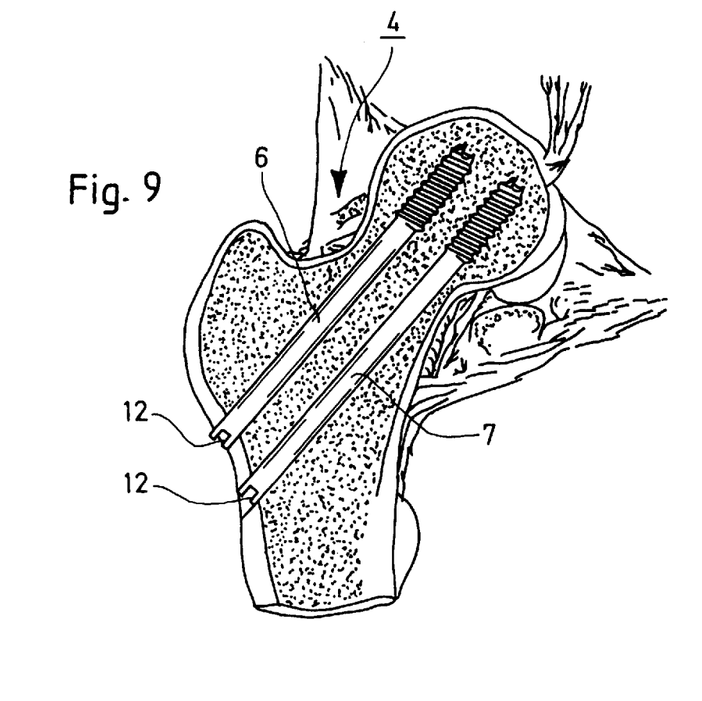
FIG. 9 is a side view of the two bone screws driven to their fixed positions in the bone fragments.

Thereby, both bone screws 6, 7 have been driven or advanced under guidance to their intended positions in the femoral neck 4 and the bone fragments 2, 3 have been fixed by means thereof. This means that the drive means 13, 14 and the guide instrument 1 can be removed (FIG. 9).

For pivoting or rotating the drive means 13, 14, a separate tommy bar 37 is preferably used. For being able to connect said tommy bar with the drive means 13, 14, each of said drive means 13, 14 is provided at the rear with two planar, bevelled surfaces, by means of which an oval end portion 38 is obtained. The tommy bar 37 has an oval end opening 39 into which the end portion 38 fits, so that said tommy bar 37 can be connected with each drive means 13, 14 for rotation thereof.

The tommy bar 37 is preferably also positionable at an arm 40 on the guide instrument 1 and can thereby be used as a handle therefor.

When the femoral neck 4 has healed, the bone screws 6, 7 can be removed by unscrewing them from their bone passages 18, 20. This can be done by connecting a drive means 13, 14 with the bone screw 6, 7, connect the tommy bar 37 with the drive means 13, 14 and then pivot or rotate the bone screw 6, 7 in an inscrewing direction (FIG. 10).

Instead of using a drive means 13, 14 for unscrewing the bone screws 6, 7, one can use the tommy bar 37 together with the screw retainer 16, which has a threaded end portion 41. This end portion can be fastened or driven into the threaded rear opening 15 of the bone screw 6, 7 for connecting the tommy bar 37 with the bone screw 6, 7 so that said bone screw can be unscrewed by means of said tommy bar 37 (FIG. 11).

The invention is not limited to the embodiment described above and shown in the drawings, but may vary within the scope of the following claims. Thus, the guide instrument 1 can be used at other bone fractures than femoral neck fractures, the bone screws 6, 7 can be of another type than shown, the guide instrument 1 can be designed for guiding more than two bone screws, the bone screws 6, 7 and/or drill steels 17, 19 and/or passages 23, 24 can have other diameters than those mentioned, the drill steels 17, 19 can be designed otherwise than described (the drill steels 17, 19 may e.g. be designed without narrow points 21), at least one thread 27, 28 can be provided around each passage 23, 24 and these threads 27, 28 can have another shape than shown if necessary for fitting in with the external threads 9 of the bone screws 6, 7 and the guide instrument 1 can have one or more other fixing portions than a fixing tip 33 of the illustrated design.

Figure 10:
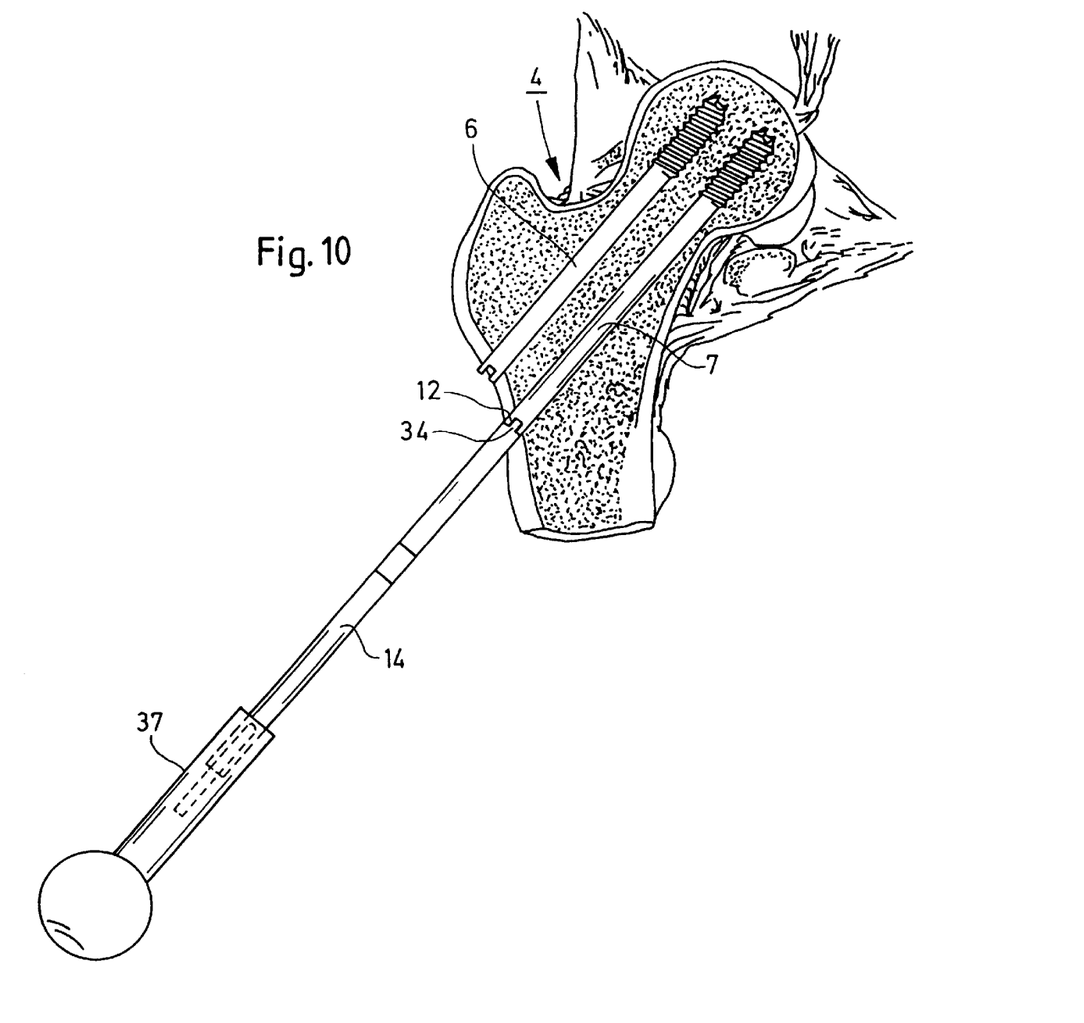
FIG. 10 is a side view of a driving means connected with a bone screw and provided with a handle for unscrewing the bone screw.
Figure 11:
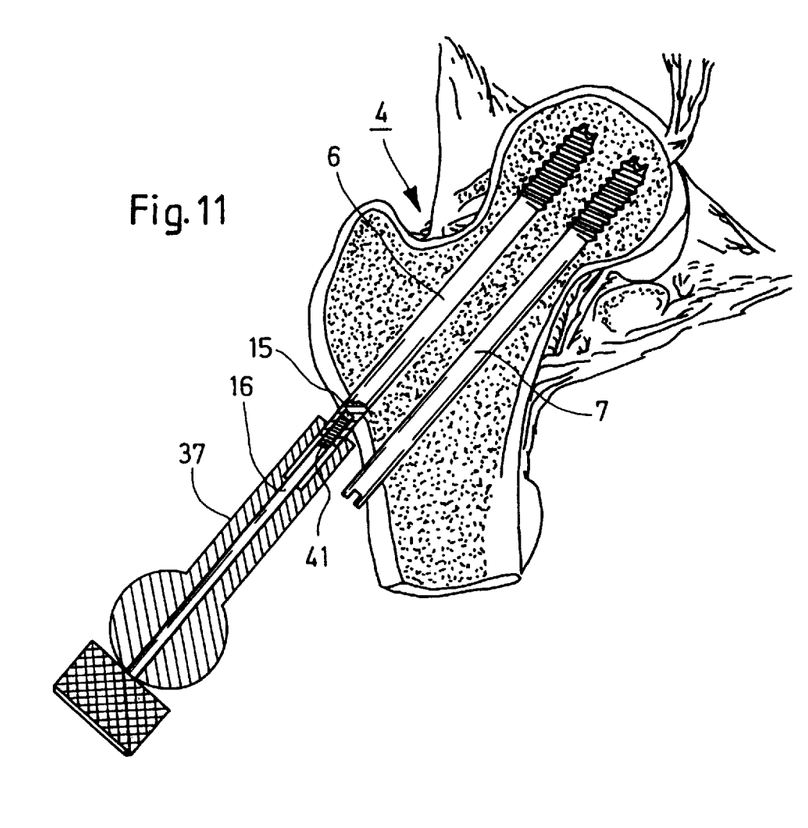
FIG. 11 is a side view of a handle located on a bone screw for unscrewing thereof from the bone fragment.

Instead of the removing members illustrated in FIG. 10 and 11 for removing or withdrawing the bone screws 6, 7, removing members of other types may be used.

I claim:

1. A set of implements for use in fixing bone fragments (2, 3) relative to each other at bone fractures by means of at least two bone screws, said set of implements comprising:

a guide instrument (1), at least two bone screws (6, 7), and at least first and second drills (17, 19)

each of said bone screws (6, 7) having a front portion (8) with external threads (9) of a given diameter (D1) and a rear unthreaded portion (10) of a given diameter (D2) smaller than said diameter (D1) of said front portion, each of said drills (17, 19) having a maximum diameter (D4) along a major portion of its length, said guide instrument (1) including a body having a first and a second passage (23, 24) and internal threads (27, 28) provided along each of said passages (23, 24), with each of said passages (23, 24) having a minimum diameter (D5) which is so sized relative to the diameter (D4) of each of said drill steels (17, 19) and to the diameter (D2) of said rear portion (10) of each bone screw (6, 7) as to enable said internal thread (27, 29) of each passage to slidable support and guide one of said drill steels (17, 19) and one of said bone screws (6, 7), at different times, for movement through said guide instrument, the internal threads (27, 28) provided along each passage (23, 24) having a root diameter (D6) which is so sized relative to the diameter (D1) of the external threads (9) on the threaded portion (8) of each bone screw (6, 7) as to enable said internal threads of said passages to threadably slidably mesh with said external threads of said bone screws to allow said threaded portion of said bone screws to be rotatably driven through said guide instrument body.

2. A set of implements according to claim 1, wherein:

said root diameter (D6) of the threads (27, 28) in the guide instrument body is 0,4–1,0 mm greater than the outer diameter (D1) of the external threads (9) on the threaded portions (8) of the bone screws (6, 7).

3. A set of implements according to claim 1, wherein:

the diameter (D5) of the first and second passages (23, 24) provided in the guide instrument body is 0,1–0,4 mm greater than said maximum diameter (D4) of said first and second drill steels (17, 19) and also 0,1–0,4 mm greater than said diameter (D2) of the unthreaded portions (10) of the bone screws (6, 7).

4. A set of implements according to claim 1, wherein:

said first and second passages (23, 24) in the guide instrument (1) have in the longitudinal direction of said passages (23, 24) straight guide surfaces (29) for guiding the first and second drill steels (17, 19) and for guiding said unthreaded portions (10) of the bone screws (6, 7).

5. A set of implements according to claim 4, wherein:

the guide surfaces (29) have a length (L) which is substantially greater than the width (B) of that part of the threads (27, 28) which separates the guide surfaces (29) from each other.

6. A set of implements according to claim 1, wherein:

each of said internal threads (27, 28) in the guide instrument body runs along a helical line (30) which extends in at least four turns around the respective one of said passages (23, 24) in the guide instrument body.

7. A set of implements according to claim 1, wherein:

each of said drill steels (17, 19) has a point (21) with a smaller diameter (D3) than the diameter (D4) of the portions (22) of the drill steel (17, 19) located behind said point (21) and that the diameter (D3) of the point 21) preferably is about half as large as the diameter (D4) of said portions (22) located behind said point (21).

8. A set of implements according to claim 1, wherein:

each of said drill steels (17, 19) has position marks (31) for determining how far in the drill steel (17, 19) has penetrated.

9. A set of implements according to claim 1, wherein:

said guide instrument further comprises a fixation tip (33) which can be brought into engagement with the bone fragment (2) in which the inlet to a bone passage (18) is located to fix the guide instrument (1) in a certain position relative to said bone fragment (2).

10. A set of implements according to claim 1, wherein:

a first passage (23) of said two passages (23, 24) in the guide instrument (1) permits retention of said guide instrument on a first drill steel (17) while said first drill steel remains seated in a first bone passage (18) drilled by said first drill steel to permit guidance of a second drill steel (19) during drilling of a second bone passage (20).

11. A set of implements according to claim 1 and further comprising:

at least one drive means (13 and/or 14) for driving at least one of said bone screws (6 and/or 7), said drive means being receivable in at least one of the passages (23 and/or 24) in the guide instrument body, said drive means (13 and/or 14) having at least one position mark (35 and/or 36) to mark that a bone screw driven by said drive means has advanced sufficiently far into the associated bone passage.

12. A set of implements according to claim 1 and further comprising:

a drive means (13) for driving at least one of said bone screws (6, 7) and receivable in at least the second passage (24) in the guide instrument (1) so that said drive means (13) can be used for retaining the guide instrument (1) in a guiding position for guiding a bone screw (7) during driving thereof into the first bone passage (18) after another bone screw (6) has been driven into the second bone passage (20) and the connection of a drive means for said another bone screw with said another bone screw (6) is maintained.

13. A set of implements according to claim 1 and further comprising:

a tommy bar (37) for unscrewing a bone screw (6, 7) from a bone passage (18, 20) and which tommy bar is releasably connectable with either one of said bone screws.

14. A set of implements according to claim 13, wherein:

said tommy bar (37) is provided as a handle on the guide instrument (1).

15. The method of using the set of implements of claim 1, wherein:

a first bone passage (18) is drilled into said bone fragments using a first one (17) of said drills guided by said first guide passage (23) of said guide instrument, while said first drill remains seated in said first bone passage (18) and in said first guide passage (23) of said guide instrument using a second one (19) of said drills guided by said second passage (24) of said guide instrument to drill a second bone passage (20) into said bone fragments, removing said second drill (19) from said second bone passage (20) and from said second aide passage (24), thereafter while said first drill remains seated in said first bone passage (18) and in said first passage (23) of said guide instrument driving one (6) of said screws through said second guide passage (24) into said second bone passage (20), removing said first drill (17) from said first bone passage (18) and from said first guide passage (23) in the guide instrument (1), and then driving a second one (7) of said screws through said first guide passage (23) and into said first bone passage (18).

* * * * *